(12) United States Patent
Agrawal et al.

(10) Patent No.: US 10,478,095 B2
(45) Date of Patent: Nov. 19, 2019

(54) SYSTEM AND METHOD FOR REAL-TIME PERSONNEL FATIGUE LEVEL MONITORING

(71) Applicant: Dharma P Agrawal, Cincinnati, OH (US)

(72) Inventors: Dharma P Agrawal, Cincinnati, OH (US); Abhinav Prakash, Cincinnati, OH (US); Suryadip Chakraborty, Cincinnati, OH (US); Anagha Jamthe, Irving, TX (US); Saibal Kumar Ghosh, Cincinnati, OH (US)

(73) Assignee: Dharma P. Agrawal, Cincinnati, OH (US)

( * ) Notice: Subject to any disclaimer, the term of this patent is extended or adjusted under 35 U.S.C. 154(b) by 1091 days.

(21) Appl. No.: 14/846,851

(22) Filed: Sep. 7, 2015

(65) Prior Publication Data
US 2016/0345865 A1    Dec. 1, 2016

Related U.S. Application Data

(60) Provisional application No. 62/166,193, filed on May 26, 2015.

(51) Int. Cl.
*A61B 5/103* (2006.01)
*A61B 5/00* (2006.01)
(Continued)

(52) U.S. Cl.
CPC .......... *A61B 5/1036* (2013.01); *A43B 3/0005* (2013.01); *A61B 5/0022* (2013.01);
(Continued)

(58) Field of Classification Search
CPC ... A61B 5/1036; A61B 5/1038; A61B 5/4023; A61B 5/6807; A61B 5/022;
(Continued)

(56) References Cited

U.S. PATENT DOCUMENTS 8,011,229 B2   9/2011 Liberman et al.
10,034,622 B1* 7/2018 Mahmoud ............ A61B 5/1038
(Continued)

OTHER PUBLICATIONS

R. Weist, E. Eils, and D. Rosenbaum, "The Influence of Muscle Fatigue on Electromyogram and Plantar Pressure Patterns as an Explanation for the Incidence of Metatarsal Stress Fractures," American Journal of Sports Medicine, Dec. 2004, vol. 32, No. 8, pp. 1893-1898, available online after Nov. 23, 2004.
(Continued)

*Primary Examiner* — Daniel L Cerioni
(74) *Attorney, Agent, or Firm* — Dorsey & Whitney LLP

(57) ABSTRACT

The present invention relates to analyzing fatigue level of users by transmitting pressure data from user's shoes wirelessly for real-time monitoring. Athletes for in body-contact games such as football, are often suddenly forced out of games due to injuries as it is often difficult to ascertain the nature of the injury on the field. The present invention enables a coach to have an ability to monitor performance of the athletes as they play, thus help in determining current level of athlete's injury, and help in preventing career threatening and/or fatal injuries. Further, pressure sensors can be used to determine fatigue detection and can be verified by readings from knock sensor, accelerometer data, etc. Variations in all such sensors for a time slice t-seconds can be used as an indicator for fatigue.

14 Claims, 4 Drawing Sheets

(51) Int. Cl.
*A43B 3/00* (2006.01)
*G06Q 50/22* (2018.01)
*G06Q 10/06* (2012.01)

(52) U.S. Cl.
CPC ...... *A61B 5/6807* (2013.01); *G06Q 10/06311* (2013.01); *G06Q 10/06398* (2013.01); *G06Q 50/22* (2013.01); *A61B 5/4023* (2013.01); *A61B 2503/10* (2013.01); *A61B 2562/0247* (2013.01); *A61B 2562/04* (2013.01)

(58) Field of Classification Search
CPC .............. A61B 2503/10; A61B 5/0022; G06Q 10/06398; G06Q 10/06311; G06Q 50/22; A43B 3/0005
USPC .......................................................... 600/595
See application file for complete search history.

(56) References Cited

U.S. PATENT DOCUMENTS

| | | | |
|---|---|---|---|
| 2004/0153007 A1* | 8/2004 | Harris | A61B 5/1038 600/587 |
| 2006/0016255 A1 | 1/2006 | Haselhurst et al. | |
| 2009/0137933 A1 | 5/2009 | Lieberman et al. | |
| 2011/0054359 A1* | 3/2011 | Sazonov | A43B 3/0005 600/595 |
| 2011/0313714 A1 | 12/2011 | Liberman et al. | |
| 2013/0013331 A1* | 1/2013 | Horseman | G06F 19/3418 705/2 |
| 2013/0032413 A1 | 2/2013 | Smith et al. | |
| 2015/0351690 A1* | 12/2015 | Toth | A61B 5/6833 600/373 |
| 2016/0000373 A1* | 1/2016 | Karavirta | G06F 19/3481 702/19 |
| 2016/0313174 A1* | 10/2016 | Lightstone | G01G 19/50 |
| 2016/0345829 A1* | 12/2016 | Kirby | G06F 19/3418 |

OTHER PUBLICATIONS http://www.livestrong.com/article/513231-frequency-of-injury-among-college-athletes/.
"Barefoot Running: Evitar lesiones cambiando nuestra forma de correr," available at http://www.buenaforma.org/2014/03/13/barefoot-running-evitar-lesiones-cambiando-nuestra-forma-de-correr/.
G. Gobbi, D. Galli, C. Carubbi, A. Pelosi, M. Lillia, R. Gatti, V. Queirolo, C. Costantino, M. Vitale, M. Saccavini, M. Vaccarezza, and P. Mirandola, "Assessment of body plantar pressure in elite athletes: an observational study," Sport Sciences for Health, Springer-Verlag Italia 2013, pp. 1038/1-6.

* cited by examiner

SYSTEM AND METHOD FOR REAL-TIME PERSONNEL FATIGUE LEVEL MONITORING

CROSS-REFERENCE TO RELATED APPLICATIONS

This application claims the benefit of U.S. Provisional Application Ser. No. 62/166,193 titled "Real-time Personnel Fatigue level Monitoring," filed on May 26, 2015. The disclosure of the above application is incorporated herein by reference in its entirety for any purpose.

FIELD OF THE INVENTION

The present invention generally relates to analyzing fatigue level of users, and particularly relates to transmitting pressure data from user's shoes wirelessly for real-time monitoring of user's fatigue level.

BACKGROUND OF THE INVENTION

When a college athlete sustains an injury one of his or her main concern is how soon he or she can return to the sport. The answer to this question is not always easy because each athlete and each injury is unique. Returning too soon can increase the risk of re-injury or developing a chronic problem that will lead to a longer recovery. Waiting too long, however, can lead to unnecessary deconditioning. Return-to-play decisions are fundamental to the practice of sports medicine but vary greatly for the same medical condition and circumstance. Although there are published articles that identify individual components that go into these decisions, there exists neither quantitative criteria for allowing an athlete to return to play nor a model for the sequence or weighting of these components within the medical decision-making process. There needs to be objective decision-based models developed for clinical use by sports medicine practitioners that take into account quantification of the forces that caused the injury and individualized, quantifiable outcomes for players attempting to return to play.

In a United States patent application 20060016255 to Haselhurst et al., sole sensors are placed to determine if foot is touching ground, provide assistance to those having difficulty in walking by transmitting sensor data to remotely placed receiver. Visual confirmation is necessary for amputation of the limb and degenerative conditions for diabetes, frostbite and obesity, and is very useful for Gait-assisted therapy.

Monitoring equilibrium of a user by putting a pressure sensor inside the shoe used as a medical scale or mat and analyzing postural state is covered in a United States patent to Liberman et al., "Methods and systems for sensing equilibrium," United States Patent No. 2009/0137933. Reading from each sensor is transmitted using any wired or wireless link Radio Frequency link (an infrared link, a Wi-Fi link, a USB link, a Fire Wire link) to a computing device for buffer before forwarding to an external device. Computing device employs a Hidden Markov Model (HMM) to determine the current and/or next postural state. There may be a number of pressure sensors in each insole, placed at a variety of locations, and possibly different numbers of sensors in each sole to provide multi-dimensional pressure information. Appropriate metrics are displayed at the medical professionals in assisting physical therapy to the patients. There are three possible dynamic states of return to present equilibrium, transition to new equilibrium, or falling down. Other states include sitting, standing, kneeling, lying down, falling, and/or other postural position of postural state (e.g., falling, standing, running, walking, etc.). The range of postural stability can be processed to determine the range of stable postural states. A unique a safe zone for every person can be determined based on a person's age, Weight, height, activity level, and/or any other type of parameter associated with posture. For stability measurement, they have used piezoresistive force sensors connected by wires to sole via communications module that provides excitation voltage and amplification, resulting in a force to voltage conversion and do not suggest any way of having a long-range wireless link. Sensors may sample the analog sensor output at a sampling rate of 100 HZ and produce digital pressure information to be stored in a 256 MB non-volatile buffer memory, periodically read by processing circuit and transmitted by Bluetooth communication network to a nearby computing device.

A recent United States patent application 20130032413 to Smith et al., introduces a system that could evaluate person's bodyweight distribution and posture for personal training and/or physical therapy where a person may have a tendency to use one part of the body over the others, causing excessive wears in that part. Thus, a lack of equilibrium in person's balance can be evaluated inaccurately. Single plated balance scale cannot identify incremental changes in person's balance that is needed for any physical therapy. This patent introduces a dual-sided scale with an independent compression sensor and the values are passed on to a hardwired computer system that also stores historical values that could indicate any changes in measured values. In another United States patent application 20110313714 to Liberman et al., postural stability of a person is determined by taking multiple readings over a period of time. By including a stability processing module, based on current and past pressure numbers, future values with an estimated probability of occurrence, can be predicted. This also helps in guessing postural stability. If the future postural happens to be unstable, the person is advised to slow down to let the walking person have a good balance. This is equally applicable to person using a can or walking using crutches. Such dynamic state representation indicates either stable state or transition to a new state of falling down.

A method for determining postural position of a person is introduced by Lieberman et al. in the United States patent "DETERMINING POSTURAL STABILITY," U.S. Pat. No. 8,011,229, and such scheme extends with two sensors at each foot (one at the toe and another in the lateral midfoot) while keeping the processing unit at the heel. So, the reading about pressures at two points of each foot and posture can be determined if someone stands on the unit. This system cannot be used for a moving person or a player.

Patents have been filed that provide simplistic static solutions to weight and posture determination of a person either in a hospital or at some fixed locations. These schemes cannot be utilized for moving people like football players for which an altogether new approach is desirable.

Starting 1988, NCAA and National Athletic Trainers' Association have been using an injury surveillance system that collects injury reports submitted by trainers for roughly 380,000 male and female college athletes. Through 2004, there were 200,000 injury reports—filed when an athlete misses a day or more of practice or competition—which works out to about 12,500 injuries per year. That number has been relatively consistent over the years (See http://www.livestrong.com/article/513231-frequency-of-injury-among-college-athletes/).

The performance of athletes in collegiate sports is very important for the reputation of universities in North America. While large sums of money are spent on recruiting the best coaches and trainers, athletes are often suddenly forced out of games due to injuries that they may have happened during training or picked up while in an actual game. In body-contact games such as football, it is often difficult to ascertain the nature of the injury since there is so much action on the field. The injuries are often brought to the attention of coaches and/or trainers when the athlete has suffered a concussion that may affect his playing abilities. The coach should also have an ability to monitor performance of the athletes as they play, thus help in determining current level of athlete's injury, and help in preventing career threatening and/or fatal injuries. Furthermore, it should be possible to monitor players during the course of a game and determine the extent of concussions arising from a normal game-play. Therefore, technological solutions enabling the monitoring of athletes' motion and physiological signals during sports and exercise are gaining increased attention as tools for preventing overload and for supporting rehabilitation in movement activities.

It is therefore an objective of the present invention to build a system and method for monitoring postural balance and stability of the athletes in real time and provide valuable feedback to the coaches so as to minimize the injury to the athletes and maximize their playing potential. It is another object of the present invention to possess capabilities to log the data for quick detection of concussion. Advances in miniaturized and wireless technology are beginning to push the capture measurement of real time game situation forces from being simulated in the training room that indicates what actually happens on the playing field. It is another object of the present invention to use wireless technology employing small sensors as it allows monitoring of kinematic, kinetic and physiological data without affecting individuals in executing their motions. It is another object of the present invention to develop a lightweight, wearable electronic force monitor to produce data for contact and injury forces, and by storing and analyzing the data, to provide the coach with a complete picture of an athlete's fitness and thus enable the coach to pick the athletes playing for the whole team.

SUMMARY OF THE INVENTION

According to the present invention, a system or method monitors the impact suffered by athletes and determine the level of postural instabilities following a concussion. The system would be versatile and be able to support other sensing devices over the same wireless transmission backbone. The data acquired by the system would be stored in a database accessible through a secure portal for analysis and feedback. This data can be used by coaches, doctors and other specialists in the field of athletic medicine in order to make informed decisions following injuries to players. As with any modern portal, the system would be completely scalable and support a wide range of devices from traditional desktop computers and laptops to handheld devices such as tablets and smart phones. This will be the ultimate step in building a comprehensive platform for enhancing athlete performance and improving their general well-being.

In one embodiment of the present invention, a shoe sole is installed with a plurality of sensors that take the reading when the subject is in motion. The sensors are connected to a mobile device or laptop computer via appropriate interface, which sends results to different devices like tablets and advanced mobile phones besides a laptop. A variety of user interfaces can be supported, for example, a website that can display the requested information. Additionally apps for various mobile platforms, such as the iOS, Android and the Windows Phone platform, would be developed that would enable the present invention to be used from these portable devices. The user interface would enable the user to logon and view physiological data pertaining to a particular individual. Controls would be provided on the user interface that would allow the user to view historical data and compare the same with the current data. If analysis of the data is required, additional web services would be called that would result in the database/analysis server computing the results and the resulting output would be rendered on the device.

According to one aspect of the present invention, pressure data are transmitted wireless and analyzed at base station in real-time. That way, the subject wearing the shoe can be active and there are no restrictions on his/her movement. It is directly applicable to football team with players wearing such shoes and the coach sitting on the sideline can monitor fatigue level of each player and make accurate decision when to make player rest and get replaced. The base station can be a laptop, iPhone or other similar devices. Decisions are made in base station. The present invention has advantages of allowing the user to wear shoes embedded with sensors and do not impose any limit on users' activities. The only limitation is that the distance from user to base station should be within wireless communication range.

Other aspects, advantages, and salient features of the invention will become apparent to those skilled in the art from the following specification and the accompanying drawings.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
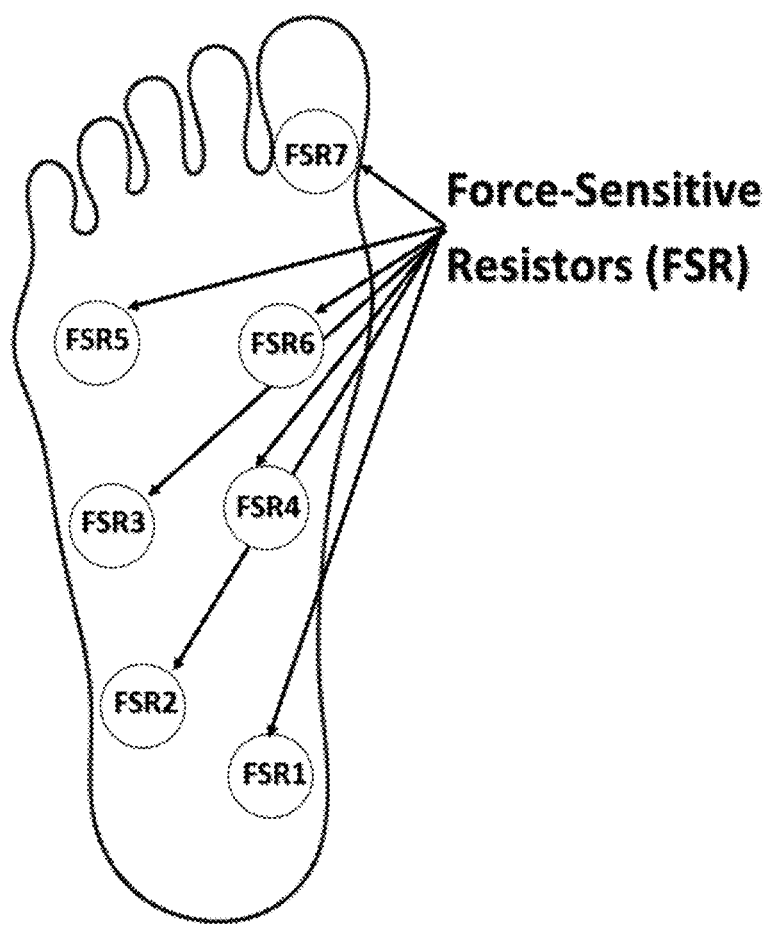
FIG. 1 shows an exemplary placement of seven sensors in a shoe sole according to one aspect of the present invention.

The present life style, especially in western hemisphere, makes people work continuously for an extended period of time. Besides emergency situations, this is true in many cases such as professional players, nurses, interns, soldiers, pilots, night-shift employees, bus and truck drivers, workers in extreme weather environments, etc. Many times, the level of tiredness could be fatal and disastrous. So, for these people to be successful, it is important to continuously monitor their fatigue level.

In one embodiment of the present invention, a plurality of sensors are placed and hidden inside shoe sole, for which the readings are transmitted wirelessly through an on-board micro-controller to a portable device within the wireless range for data logging, storing and analysis. According to one aspect of the invention, with reference to FIG. 1, seven round Force-Sensitive Resistors (FSRs) and a micro-controller are installed onboard inside the sole. The microcontroller, such as Teensy 3.1 32-bit ARM Cortex-M4 platform, which is powerful and extreme small factor, is connected to the FSRs and configured to select any of the FSR readings to be transmitted and send control signals to actuators in a mobile compact environment. The software backbone for the Teensy is Arduino platform with Arduino Platform libraries, which is an open-source platform that provides the capability of programming in C language.

Teensy provides several digital and analog inputs accommodating all of the required sensor inputs. According to one aspect of the present invention, this micro-controller platform is paired with a low energy wireless interface, such as Bluefruit LE—Bluetooth Low Energy (BLE 4.0), which provides wireless connectivity to the micro-controller to an iOS or Android based device to transmit the sensor readings over a wireless Bluetooth 4.0 Low Energy connection to any entity with Bluetooth capability such as laptop, cell phone, tablet (e.g. iPad) and other portable devices (e.g. iPod). These sensor readings are gathered by the Teensy board and all analog readings are automatically converted into digital values by the built-in analog to digital converter. Then these values are passed on to the Bluefruit Bluetooth board over the wired connections, which are further transmitted to a paired Bluetooth 4.0 LE capable (for example, iOS or Android or other OS support present) device over the Bluetooth wireless channel.

According to another aspect of the present invention, a longer range wireless interface, such as the Adafruit HUZ-ZAH CC3000 WiFi, is provided. The Adafruit HUZZAH CC3000 WiFi is totally compatible with Arduino Platform and data can be pushed as fast or slow as needed to a longer distance of approximately 350 feet as compared to Bluefruit LE 2.0 (20 feet). It has an asynchronous connection and supports 802.11b/g, open/WEP/WPA/WPA2 security, TKIP & AES. TCP and UDP in both client and server modes are possible with up to 4 concurrent sockets. While WiFi consumes more power than Bluetooth, the power can be saved by transferring the sensor data only when the player is playing, which playing state can be determined by the onboard micro-controller based on the readings of the force sensor data.

WiFi and Bluetooth add-on boards can perform independently, thus the absence or presence of one does not affect the performance of the other. According to one aspect of the present invention, WiFi is kept in sleep mode most of the times and consumes almost negligible power. It is strictly invoked by the onboard micro-controller under one of the two conditions: 1) unavailability of Bluetooth channel due to any reason, for example, congestion or hardware issue, etc.; 2) very high bandwidth demand greater than 1 Mbps. While both of these conditions are highly unlikely to occur, it is advantageous to have a backup while collecting sensitive health data to ensure its fast availability for decision making under real-time dynamic situations.

In one embodiment of the present invention, for applications requiring under 1 Mbps bandwidth, the newer BLE 4.0 is preferred because it has been proven to be a better performer than other wireless transmission technologies available in the market like WiFi Direct etc. Particularly, BLE 4.0 is advantageous as compared to BLE 2.0 (used in available smart watches) because of its 1) Low Power Consumption: Literally runs for several days without loss on coin batteries; 2) Range: Upwards of 330 feet (100+ meters); 3) Latency: Connection setup and data transfer as low as 3 ms, allowing an application to establish a connection and then transfer authenticated data in a few milliseconds for a short burst before quickly disconnecting the connection; 4) Efficient Host Control: BLE 4.0 allows the host to go to sleep mode for very large durations when not required and still successfully waking it when required; 5) Other Extra Features (as may be available in other technologies): 24-bit CRC on all packets, AES-128 encryption, 32-bit addressing topology that can handle millions of devices. Currently available smart watch costs over $100, employs BLE 2.0, which has limited range of 20 feet, low bandwidth, and high power consumption.

Figure 3:
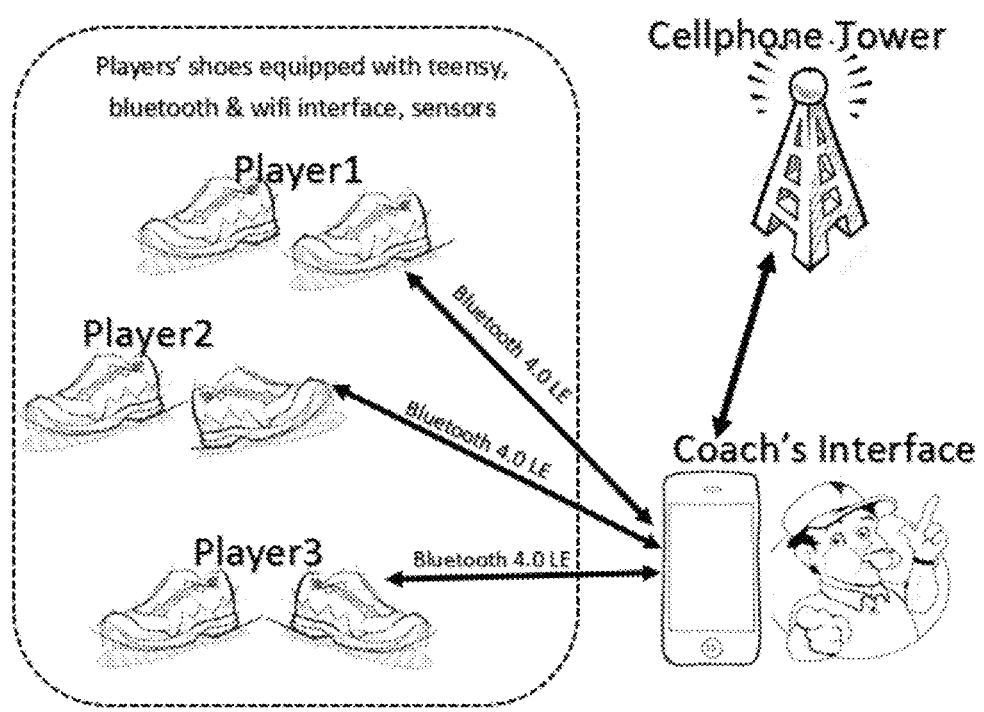
FIG. 3 shows device communications according to one aspect of the present invention.

According to one aspect of the present invention, the various units (e.g. the micro-controller, the Bluetooth module and/or WiFi interface) should be hardwired together and then embedded in the shoe. For example, a Mexican wicker shoe (such as shown in FIG. 3) is selected as our wearable smart device. The wicker based open weave provides multiple benefits like ease of wiring due to several access holes and the capability of weaving the wiring along with the wicker weave, hiding several sensors inside the weave, keeping all the electronic components air cooled hence preventing frequent failure from overheating issues. Other types of shoes can also accommodate the various units aforementioned as would one with ordinary skill in the art.

Figure 2:
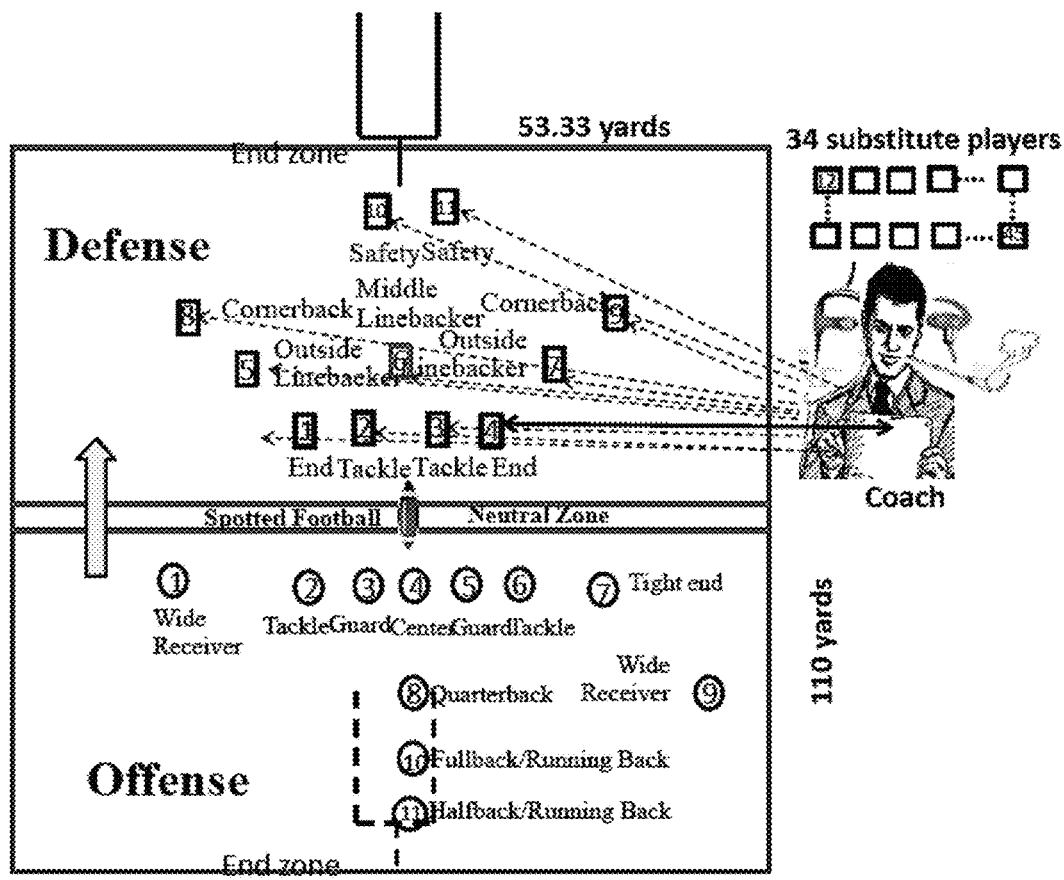
FIG. 2 shows a scheme diagram of football player's fatigue detection according to one aspect of the present invention.

With reference to FIGS. 2 & 3, the fatigue level of an individual is determined by the monitoring station. For example, players play in the field and vital pressure values are transmitted to the coach monitoring on the side lines. The coach carrying an iPhone or similar portable device can get the data from pressure sensors of both the shoes of a selected player and analyze it to determine fatigue level of the player. According to one aspect of the present invention, the coach can use the portable device to analyze the data and determine fatigue level of each of the players. Alternatively, the portable device is used to send data to a central base station for further processing and getting feedback about the status of a given player.

In determining the muscle fatigue, the work by Weist et al. in "The Influence of Muscle Fatigue on Electromyogram and Plantar Pressure Patterns as an Explanation for the Incidence of Metatarsal Stress Fractures," American Journal of Sports Medicine, December 2004, vol. 32, no. 8, pp. 1893-1898, available online after Nov. 23, 2004, suggested use of 10 sensors in each shoe and determining difference in pressure from two feet. The pressure pattern indicates EMG (Electromyography) fatigue level. According to one aspect of the present invention, seven (7) sensors are adopted for use in each shoe (as shown in FIG. 1) because these 7 pressure sensors show difference in reading between two feet while remaining three remain unchanged.

Figure 4:
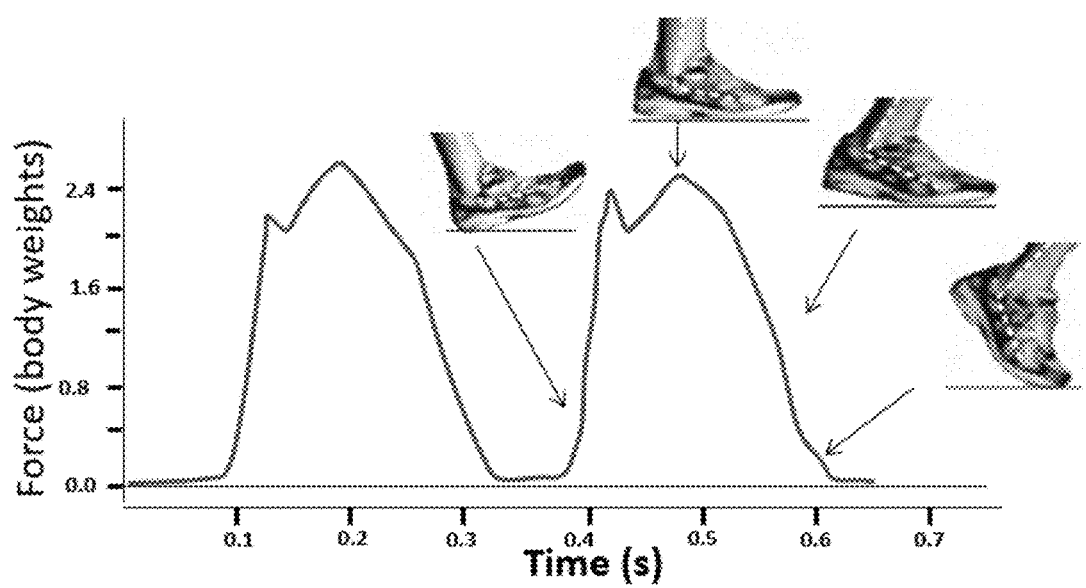
FIG. 4 shows variations of body force at different angles of foot.

According to one aspect of the present invention, whether an individual is walking, resting, climbing up stairs, running, etc., can be determined by the monitoring unit as variation in the pressure will indicate that phenomenon. This is shown in FIG. 4, indicating co-relation between the body forces at different angles of the shoe worn by an individual, i.e., the transient body pressure on each leg depends on the angle of the toe as illustrated in FIG. 4 (See "Barefoot Running: Evitar lesiones cambiando nuestra forma de corer," at http://www.buenaforma.org/2014/03/13/barefoot-running-evitar-lesiones-cambiando-nuestra-forma-de-correr/). However, under steady state, people exert different amount of pressures on two legs if a person suffers from Parkinson's disease. Such imbalance in exerted force has also been observed in football games (G. Gobbi et al, "Assessment of body plantar pressure in elite athletes: an observational study," Sport Sciences for Health, Springer-Verlag Italia 2013, pp. 1038/1-6), making the present invention particular advantageous because among various games, football still has the highest injury rate with 36 injuries per 1,000 male athletes (See http://www.livestrong.com/article/513231-frequency-of-injury-among-college-athletes/). The present invention not only helps coach use substitute players when needed but also serves players in minimizing their injuries. The present invention can also be used for other fast sports such as soccer, ice hockey, basketball, etc. The present invention can also be used in determining fatigue levels in soldiers, medical interns, and nurses.

Besides relaying real-time data from seven pressure/force sensors, additional sensors of vibration, acceleration, temperature and humidity can also be installed, and the readings of these sensors are also obtained with the micro-controller, such as the Teensy board. All the data logging, analysis and filtering is done at the base station, such as an iOS or Android device which can be an iPad, cellphone, or any tablet device. According to one aspect of the present invention, prior medical info regarding correlations between health condition and data patterns of such data can be used. According to another aspect of the present invention, the vibration, acceleration, temperature or humidity data can be used as a biometric signature, which can be used for security hash function being unique for a test subject and linked to various health anomalies. According to another aspect of the present invention, these data in additional to readings of pressure sensors are used to reconfirm decisions about the electromyography (EMG) and fatigue level determined in the base station based on the readings from pressure sensors.

The description of the invention is merely exemplary in nature and, thus, variations of the above disclosed embodiments can also be made to accomplish the same functions. For example, sensor data can be transmitted to the base station constantly as they are collected. According to another aspect of the present invention, all or part of the data provided by pressure sensors for each player can be analyzed by the micro-controller inside the shoe. Then, if the fatigue level exceeds a predefined threshold value, a distress signal is sent to the base Station. That way, data transferred to base station is minimized as there are many players on the field and could be sending data at the same time.

Still further, other sensors can be used to calculate other measurement values as bases of determining fatigue level. The basic idea is just to identify the shape of the indicators and matching it to current health condition of the test subject. Besides the identification of occurrence of fatigue level based on the feedback from pressure sensors, as shown in FIG. 4, we can identify the variation, if any, at other sensor data available for example Piezo (Knock Sensor), accelerometer data, etc. All such variations in sensor data linked to fatigue can be drawn as a curve versus time. The presence of such variations for a time slice t-seconds at all such sensors can be tied together as an indicator set for fatigue. Once we have such indicator set data recorded, when such a condition reoccurs our detection time will be t seconds under which our shoe can positively report such an occurrence. Additionally, we can minimize t in order to guarantee a fast response time while keeping false positives under a certain required limit. It should be noted that time t will have a lower threshold value here during which all indicator set sensors show variation matching our recorded pattern earlier.

According to one embodiment of the present invention, with reference to the table below, the dynamic changes and combinations of all these values can give very interesting insight into the health state including fatigue level of our test subject.

| Sensors | Measurements |
| --- | --- |
| 1. Temperature & Humidity Sensor | 1. The arch in the foot of the test subject |
| 2. Triple-axis analog accelerometer - for measuring motion and tilt | 2. The amount of knock/vibration absorbed by the foot when it falls on the ground |
| 3. Hall Effect sensor - for sensing a magnet used with a Magnet - for use with the Hall Effect or as a compass using the gravitational force | 3. Altitude |
| 4. Piezo - Used as a knock sensor | 4. Orientation |
| 5. Ball tilt sensor - for sensing orientation | 5. Direction of travel |
| 6. Photo cell sensor - for sensing light | 6. Distance between the two feet |
| 7. IR sensor - for sensing infrared light pulsing at 38 KHz | 7. Amount of pronation |
| 8. Adafruit Ultimate GPS Breakout - 66 channel w/10 Hz updates (Version 3) | 8. Angular momentum at the ankle |
| 9. Adafruit 10-DOF IMU Breakout - 3 axes of accelerometer data, 3 axes gyroscopic, 3 axes magnetic (compass), barometric pressure/altitude and temperature | 9. Humidity giving an idea of proportional sweat levels |
| 10. Bend Sensor: long strip sensor that gives the approx. how much its being bend | 10. Temperature changes |
| | 11. Shape of the foot fall individual and relative to each other |

With help of these sensor reads we can closely monitor any change in motion of complete foot movement while running, walking, standing or any combination of such states.

Still further, while some sensors are sensing the same data, they have been carefully selected as some sensors are providing analog reading while others a digital read. The duplicated readings can be used to back up other readings for verification purposes as some sensors are really cheap and can tend to be unreliable at times. Furthermore, there is an analog to digital signal conversion on the mainboard Teensy for certain applications processing the data. In case of availability of both analog and digital signal reads a simple piece of code can query individual sensors and easily analyze and identify if such a conversion generated any level of error in computation or just a plain false read.

Redundancy validates data. Availability of multiple sensor data for observing the same quantity assures that we get most accurate values. Additionally, it also helps us identify faulty sensors and generate a system error. Further, different sensors are designed technologically differently to observe the same value, for example, we use a ball tilt sensor for orientation detection as well as we have an accelerometer too for a similar purpose. In such a case, both values can be used to validate the data and minimize the reading error. The ball tilt sensor gives an analog output in terms of voltage drop while the accelerometer is capable of generating a digital output. In utilizing the redundancy of sensor data, for example, the main board Teensy has two inbuilt ADC (Analog to Digital Converters) in case we want to query an analog sensor in real-time the value is automatically converted to digital. Such a conversion can lead to an added error known as quantization error. In presence of multiple sensor data such an error can be filtered out.

Still further variations, including combinations and/or alternative implementations, of the embodiments described herein can be readily obtained by one skilled in the art without burdensome and/or undue experimentation. Such variations are not to be regarded as a departure from the spirit and scope of the invention.

What is claimed is:
1. A system for embedding in a shoe and monitoring fatigue level of a subject, wherein said shoe having a sole, comprising:

a plurality of sensors disposed in the shoe sole;

a micro-controller communicatively connecting to said plurality of sensors and configured to receive readings of said plurality of sensors, and is further configured to validate the readings of a first sensor of the plurality of sensors with readings of a second sensor, wherein the first sensor of the plurality of sensors is a ball tilt sensor configured to detect orientation of the subject to generate first sensor data and the second sensor is an accelerometer configured to generate second sensor data used to reduce an error in the first sensor data; and a wireless interface communicatively connecting to said micro-controller and configured to send the readings of said plurality of sensors wirelessly to a base station, wherein said base station determines the fatigue level of the subject based on at least a portion of the readings of said plurality of sensors transmitted by the wireless interface.

2. The system of claim 1, wherein the plurality of sensors comprise 7 sensors.

3. The system of claim 1, wherein the base station is a portable device.

4. The system of claim 1 further comprises an array of additional sensors comprising a vibration sensor, a temperature sensor, a humidity sensor and an acceleration sensor, wherein said micro-controller is configured to receive readings of the said array of additional sensors, wherein said wireless interface is configured to transmit said readings wirelessly to the base station for determining a health anomaly based on comparing a biometric signature and a security hash function unique to the subject, wherein the biometric signature is based on the readings of at least one sensor in said array of additional sensors.

5. A shoe for monitoring fatigue level of a subject, comprising:

a shoe sole disposing a plurality of sensors therein;

a micro-controller communicatively connecting to said plurality of sensors and configured to receive readings of said plurality of sensors, and is further configured to validate the readings of a first sensor of the plurality of sensors with readings of a second sensor, wherein the first sensor of the plurality of sensors is a ball tilt sensor configured to detect orientation of the subject to generate first sensor data and the second sensor is an accelerometer to generate second sensor data used to reduce an error in the first sensor data; and a wireless interface communicatively connecting to said micro-controller and configured to send the readings of said plurality of sensors wirelessly to a base station, wherein said base station determines the fatigue level of the subject based on at least a portion of the readings of said plurality of sensors transmitted by e wireless interface.

6. The shoe of claim 5, wherein the plurality of sensors comprise 7 sensors.

7. The shoe of claim 5, wherein the base station is a portable device.

8. The shoe of claim 5 further comprises an array of additional sensors comprising a vibration sensor, a temperature sensor, a humidity sensor and an acceleration sensor, wherein said micro-controller is configured to receive readings of the said array of additional sensors, wherein said wireless interface is configured to transmit said readings wirelessly to the base station for determining a health anomaly based on comparing a biometric signature and a security hash function unique to the subject, wherein the biometric signature is based on the readings of at least one sensor in said array of additional sensors.

9. A method for monitoring fatigue level of a subject using a shoe having a sole, said shoe comprising a plurality of sensors embedded in the shoe sole; a micro-controller connecting to said plurality of sensors and is configured to validate the readings of a first sensor of the plurality of sensors with readings of a second sensor, wherein the first sensor of the plurality of sensors is a ball tilt sensor configured to detect orientation of the subject to generate first sensor data and the second sensor is an accelerometer to generate second sensor data used to reduce an error in the first sensor data; and a wireless interface connecting to said micro-controller, said method comprising the step of:

receiving, by said micro-controller, readings of said plurality of sensors;

sending, by said wireless interface, the readings of said plurality of sensors wirelessly to a base station; and determining, by said base station, the fatigue level of the subject based on the reading of said plurality of sensors.

10. The method of claim 9, wherein the plurality of sensors comprises 7 sensors.

11. The method of claim 9, wherein the base station is a portable device.

12. The method of claim 9 further comprises calculating a player state of the subject based on the received readings of said plurality of sensors, wherein the player state comprises at least playing and nonplaying states, and the sending of readings of said plurality of sensors wirelessly to the base station is invoked only when the calculated player state is indicative of a playing state.

13. The system of claim 1, wherein the first sensor is configured to generate the first sensor data in an analog format and the second sensor is configured to generate the second sensor data in a digital format, and wherein the error in the first sensor data is a quantization error.

14. The system of claim 5, wherein the first sensor is configured to generate the first sensor data in an analog format and the second sensor is configured to generate the second sensor data in a digital format, and wherein the error in the first sensor data is a quantization error.

* * * * *